United States Patent
Levy et al.

(10) Patent No.: US 8,342,172 B2
(45) Date of Patent: Jan. 1, 2013

(54) INSTRUMENTED METERED-DOSE INHALER AND METHODS FOR PREDICTING DISEASE EXACERBATIONS

(75) Inventors: Bruce D. Levy, West Roxbury, MA (US); Michael S. Singer, Newton Centre, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 788 days.

(21) Appl. No.: 12/525,540

(22) PCT Filed: Feb. 3, 2008

(86) PCT No.: PCT/US2008/052869
§ 371 (c)(1),
(2), (4) Date: Aug. 1, 2009

(87) PCT Pub. No.: WO2008/112353
PCT Pub. Date: Sep. 18, 2008

(65) Prior Publication Data
US 2010/0094099 A1 Apr. 15, 2010

Related U.S. Application Data

(60) Provisional application No. 60/899,404, filed on Feb. 5, 2007.

(51) Int. Cl.
*A61M 11/00* (2006.01)

(52) U.S. Cl. .......... 128/200.23; 128/200.14; 128/200.19

(58) Field of Classification Search . 128/200.11–200.24, 202.13, 203.14–203.15; 700/281, 275
See application file for complete search history.

(56) References Cited

U.S. PATENT DOCUMENTS

| 5,167,506 A | 12/1992 | Kilis et al. |
| 5,337,615 A | 8/1994 | Goss |
| 5,363,842 A | 11/1994 | Mishelevich et al. |
| 5,477,849 A | 12/1995 | Fry |
| 5,593,390 A | 1/1997 | Castellano et al. |
| 5,676,129 A | 10/1997 | Rocci, Jr. et al. |
| 6,014,429 A | 1/2000 | LaPorta et al. |

(Continued)

FOREIGN PATENT DOCUMENTS

EP 0 667 168 A1 8/1995

(Continued)

OTHER PUBLICATIONS

International Search Report for PCT/US2008/052869 filed Feb. 3, 2008.

(Continued)

*Primary Examiner* — Glenn Richman
(74) *Attorney, Agent, or Firm* — Law Office of: Michael A. Sanzo, LLC (57) ABSTRACT

The present invention is directed to devices, systems, and methods for monitoring inhaled drug usage to predict when an acute attack or exacerbation of a disease, such as a respiratory disease, is imminent. Instrumented inhalers that use modular designs with standard components are disclosed, as are systems for monitoring the instrumented inhalers. Also disclosed are methods for determining whether or not a patient's inhaled drug usage pattern indicates that an acute attack or disease exacerbation is imminent, and notifying appropriate medical personnel of any usage patterns indicative of an attack or disease exacerbation. If such an attack or exacerbation is imminent, additional therapeutic agents may be dispensed to the patient or other interventions made.

16 Claims, 6 Drawing Sheets

U.S. PATENT DOCUMENTS

| | | | |
|---|---|---|---|
| 6,125,844 A | 10/2000 | Samiotes | |
| 6,138,669 A | 10/2000 | Rocci, Jr. et al. | |
| 6,202,642 B1 | 3/2001 | McKinnon et al. | |
| 6,223,746 B1 | 5/2001 | Jewett et al. | |
| 6,532,955 B1 | 3/2003 | Ashurst et al. | |
| 6,582,728 B1 | 6/2003 | Platz et al. | |
| 7,458,373 B2 * | 12/2008 | Nichols et al. | 128/203.15 |
| 7,926,484 B2 * | 4/2011 | Dhuper et al. | 128/203.15 |
| 8,056,556 B2 * | 11/2011 | Childers et al. | 128/200.14 |
| 2005/0172958 A1 | 8/2005 | Singer et al. | |
| 2006/0066731 A1 | 3/2006 | Zhou | |

FOREIGN PATENT DOCUMENTS

| | | |
|---|---|---|
| GB | 2 262 452 | 6/1993 |
| WO | WO 93/12823 | 7/1993 |
| WO | WO 95/07723 | 3/1995 |
| WO | WO 97/33640 | 9/1997 |
| WO | WO 01/24690 A2 | 4/2001 |

OTHER PUBLICATIONS

Written Opinion of the International Searching Authority for PCT/US2008/052869 filed Feb. 3, 2008.

Screen shots from iMetrikus website obtained in 2005; www.imetrikus.com.

Screen shots from iMetrikus website obtained in 2009; www.imetrikus.com/pro_AW.html.

Cairns, "Acute Asthma Exacerbations: Phenotypes and Management," *Clin. Chest Med.* 27:99-108 (Mar. 2006).

Chan-Yeung, et al., "Changes in Peak Flow, Symptom Score, and the Use of Medications During Acute Exacerbations of Asthma," *Am. J. Respir.Crit. Care Med.* 154:889-893 (1996).

Gibson, et al., "Using Quality-Control Analysis of Peak Expiratory Flow Recordings to Guide Therapy for Asthma," *Ann. Intern. Med.* 123:488-492 (1995).

Hessel, et al., "Risk Factors for Death From Asthma," *Ann. Allergy Asthma Immunol.* 83(5):362-368 (Nov. 1999).

Marosi, et al., "Improving Pediatric Asthma Patient Outcomes by Incorporation of Effective Interventions," *J. Asthma* 38(8):681-690 (2001).

Martin, et al., "Assessment of the AirWatch Lung Function Monitoring System," *J Allergy Clin. Immunol.* 103(3)(Part 1):535-536 (Mar. 1999).

Tovar, et al., "Monitoring Pulmonary Function in Asthma and COPD: Point-of-Care Testing," *Ann. Pharmacother.* 38:126-133 (Jan. 2004).

* cited by examiner

INSTRUMENTED METERED-DOSE INHALER AND METHODS FOR PREDICTING DISEASE EXACERBATIONS

CROSS-REFERENCE TO RELATED APPLICATIONS

The present application is U.S. national stage of international application PCT/US2008/052869, which had an international filing date of Feb. 3, 2008, and which was published in English under PCT Article 21(2) on Sep. 18, 2008. The application claims the benefit of U.S. Provisional Patent Application No. 60/899,404, filed on Feb. 5, 2007, the contents of which are hereby incorporated by reference herein in their entirety.

STATEMENT REGARDING FEDERALLY-FUNDED RESEARCH AND DEVELOPMENT

The United States Government may have a property interest in this application by virtue of a research grant provided to the inventors. The grant was provided by the Department of Defense and is USAMRAA Grant No. DAMD17-02-2-0006

FIELD OF THE INVENTION

The present invention is directed to a medical device for monitoring the administration of drug to a patient by inhalation. In addition, the invention includes systems and methods for treating patients, particularly asthma patients, using remote monitoring of drug usage to determine when an exacerbation is imminent.

BACKGROUND OF THE INVENTION

Over twenty million Americans suffer from asthma or chronic obstructive pulmonary disease (COPD). These diseases are characterized by periods of relative normalcy punctuated by acute attacks (exacerbations) that may be severe enough to require hospitalization. Typically, an attack is preceded by a progressive increase in a patient's use of "rescue" medication to alleviate respiratory difficulties and a decrease in lung function, as measured by peak expiratory flow rate. These changes usually occur several days or weeks before an attack and can serve as a signal for initiating preemptive treatment. Unfortunately, patients often lack the time or resolve to keep accurate records of drug usage. As a result, they may not become aware that their condition is deteriorating until it is too late to prevent an attack requiring urgent medical attention. Also, pediatric, elderly, or impaired patients may lack the capacity for carefully monitoring changes in drug use patterns.

Many different types of inhalation devices have been developed and used by respiratory patients for delivering a carefully controlled dosage of medication (see, e.g., U.S. Pat. Nos. 6,223,746; and 6,532,955). Some of these devices have microprocessors and sensors for counting the number of doses administered (U.S. Pat. Nos. 6,138,669; and 5,593,390) or have other adaptations to improve delivery characteristics (U.S. Pat. No. 5,477,849). However, most continue to rely upon patients to monitor their own drug use patterns.

To the extent that devices that can be used to detect and monitor patient self-administration of inhaled drugs have been described in the prior art (e.g., WO01/024690; U.S. Pat. No. 5,363,842), they are typically used to monitor patient compliance with physician instructions, or to ensure that a patient receives no more than a certain dose of a medication. Generally, there has not been a focus on monitoring inhaled drug usage to recognize when a patient's condition is likely to be deteriorating.

Moreover, in the existing devices, the mechanism for detecting that a dose has been dispensed is usually within the device, often in a position in which it can be easily fouled by dirt or accumulated medication. The positioning of the detection mechanism often makes the design of the devices relatively complex, and increases the possibility of failure. Monitoring devices that are more robust and more compatible with conventional types of inhalers would be beneficial.

SUMMARY OF THE INVENTION

Aspects of the present invention provide devices, systems, and methods for monitoring patient inhaled drug usage to predict whether or not an acute attack or exacerbation of a chronic disease or condition is imminent. As one example, the disclosed devices, systems, and methods may be particularly useful in the treatment of asthma.

One aspect of the invention provides an instrumented metered dose inhaler with an inhaler portion and a sensor/transmitter portion. The inhaler portion allows the patient to self-administer an inhaled dose of a drug, such as a short-acting bronchodilator. The sensor/transmitter portion, which is external to the inhaler portion, registers that a dose has been dispensed and transmits that information wirelessly to a remote station. In one embodiment, the inhaler portion may be coupled to the sensor/transmitter portion by a simple mechanical coupling. For example, in one embodiment, a cap or lip may be fitted to the inhaler's medication canister, such that when the medication canister is depressed to dispense a dose, the cap or lip depresses and actuates an electrical switch, thus indicating that a dose has been dispensed. In some embodiments, the sensor/transmitter portion may be easily added to a conventional inhaler, allowing existing inhalers to be retrofit with instrumentation for monitoring.

Another aspect of the invention relates to a system for predicting disease exacerbations based on inhaled drug usage patterns. The system comprises one or more instrumented metered dose inhalers described above and a monitoring system. The monitoring system receives information regarding dispensed doses from the one or more inhalers and associates that information with patient records. Either or both of the inhalers and the monitoring system may be adapted to analyze the information from the inhalers to determine if any drug usage patterns indicate that an acute attack or disease exacerbation is imminent.

Yet another aspect of the invention relates to methods for predicting disease exacerbations based on inhaled drug usage patterns. The methods involve collecting data on usage of a first inhaled therapeutic agent by a patient essentially in real time as doses of the first inhaled therapeutic agent are dispensed, for example, using an instrumented metered-dose inhaler of the type described above, analyzing the data, and notifying medical personnel if any drug usage patterns indicate that an acute attack or disease exacerbation is imminent. In some embodiments, a second therapeutic agent or another form of intervention may be administered if an acute attack or disease exacerbation is imminent. The second therapeutic agent may be an inhaled corticosteroid, an oral corticosteroid, a leukotriene modifier, a long acting beta$_2$ agonist or a methylxanthine.

Other aspects, features, and advantages of the invention will be set forth in the description that follows.

BRIEF DESCRIPTION OF THE DRAWINGS

The invention will be described with respect to the following drawing figures, in which the same reference numerals will refer to the same features throughout the figures, and in which.

DETAILED DESCRIPTION OF THE INVENTION

Figure 1:
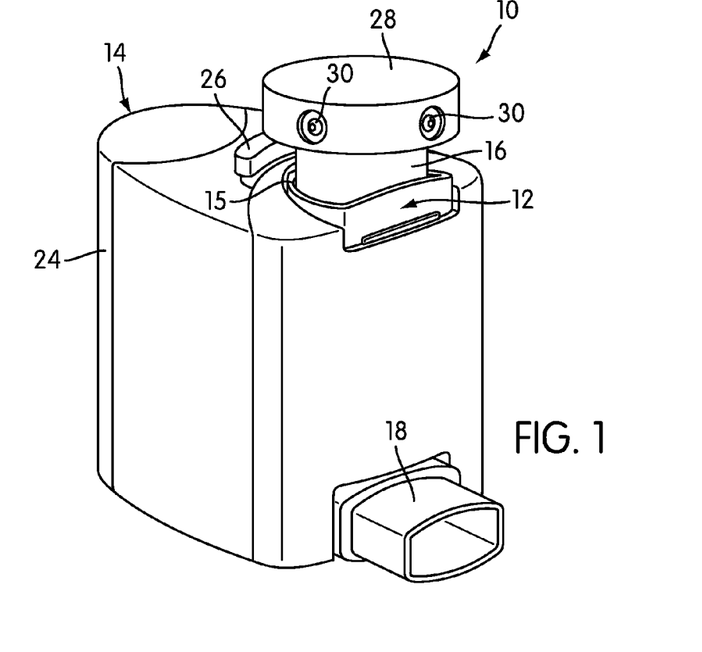
FIG. 1 is a perspective view of an instrumented metered-dose inhaler according to one embodiment of the invention.
Figure 2:
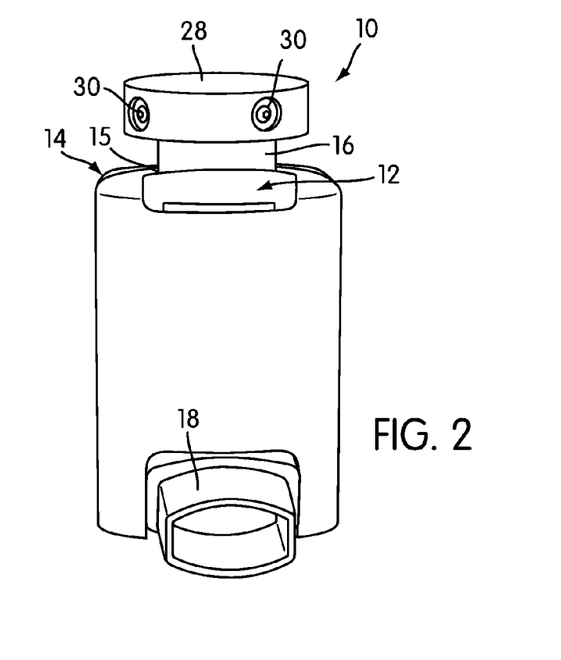
FIGS. 2-3 are front and side elevational views, respectively, of the inhaler of FIG. 1.

FIG. 1 is a perspective view of an instrumented metered-dose inhaler, generally indicated at 10, according to one embodiment of the invention. The metered-dose inhaler 10 includes an inhaler portion 12 and a sensor/transmitter portion 14.

For the purposes of the present application, the term "metered dose inhaler" will include both inhalers that deliver a liquid aerosol and dry powder inhalers. The illustrated inhaler 10 is configured for a liquid medication, such as albuterol, but other embodiments of the inhaler 10 may be configured for other types and sizes of inhalers.

Figure 4:
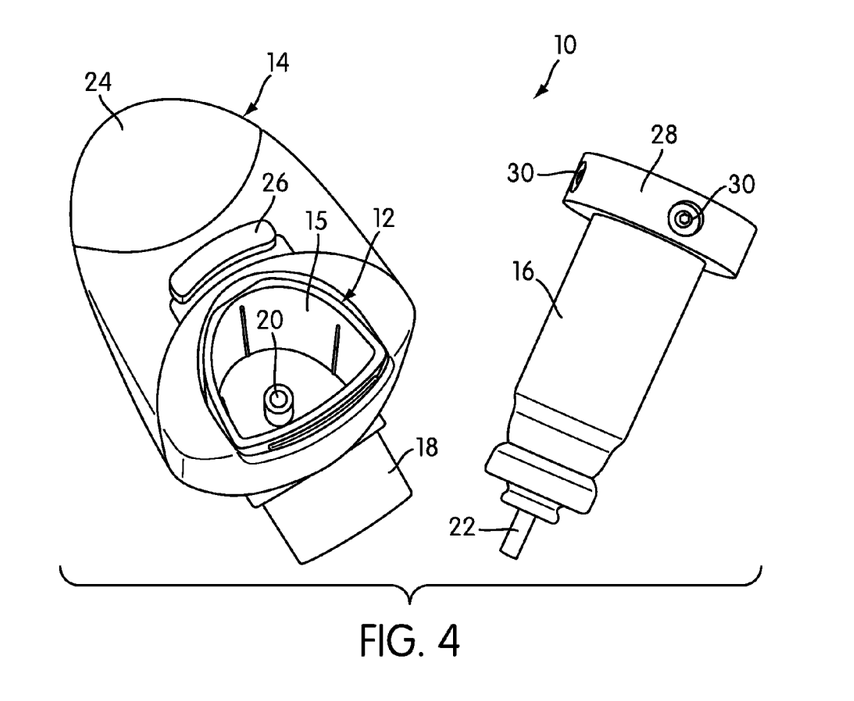
FIG. 4 is a top plan view of the inhaler of FIG. 1, with the medication canister disconnected and shown separately.
Figure 5:
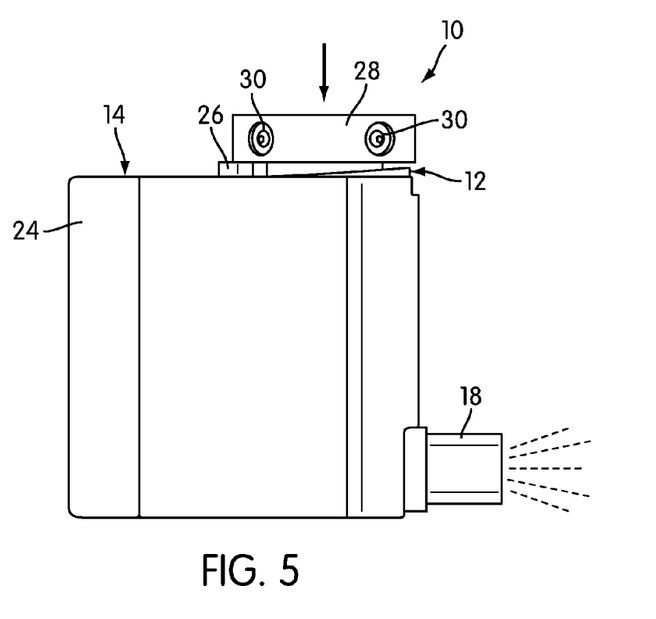
FIG. 5 is a side elevational view of the inhaler similar to the view of FIG. 3, illustrating the actuation of the device to dispense a dose of the drug.

The inhaler portion 12 of the illustrated embodiment is essentially a standard, L-shaped inhaler with a medication reservoir compartment 15 for a medication reservoir or canister 16, and a mouthpiece 18 for inhalation. Between the compartment 15 housing the medication canister 16 and the mouthpiece 18 is a flow pathway including a conventional flow chamber (not shown in the figures) that disperses the medication and mixes it with air as it is administered. FIG. 4 is a top plan view of the inhaler 10 with the medication canister 16 removed from the compartment 15. The opening 20 to the flow pathway is visible in FIG. 4.

In embodiments of the invention, the inhaler portion 12 typically has a movable part that moves between a dispensing position, in which the inhaler portion 12 is actuated to dispense a dose of medication, and a non-dispensing position, in which medication does not flow from the medication reservoir compartment 15 to the mouthpiece 18. The movable part is typically biased toward the non-dispensing position. The movement of the moveable part may be linear, rotational, or of any other type. The movable part is generally coupled to a valve or other structure that is operable to release a flow of medication. In the illustrated embodiment, the canister 16 acts as the movable part, although in other embodiments of the invention, rods, levers, tabs, and hinged, rotatable portions may all be used as moving parts.

The canister 16 is generally of a conventional type and typically contains a supply of pressurized medication with a built-in valve. The canister 16 is installed in its compartment 15 such that its nozzle 22 bears against the opening 20 to the flow chamber. When the canister 16 is depressed downwardly, a dose of the drug is aerosolized and propelled into the flow chamber, to be inhaled by the patient through the mouthpiece 18. During the process of dispensing a dose, air may be drawn into the inhaler portion 12 and mixed with the medication in the conventional way. Other embodiments of the invention may use other types of medication reservoirs and other methods of dispensing doses.

Generally speaking, if the patient's underlying condition is asthma, the medication will be a bronchodilator, typically a short-acting beta$_2$ agonist, such as albuterol; bitolterol mesylate; levalbuterol; metaproterenol sulfate; pirbuterol acetate; and terbutaline sulfate. As will be described below in more detail, if it appears that a patient is approaching an acute attack, there are several second drugs that may be given in an attempt to avert it or reduce its severity. These include long acting beta$_2$ agonists (e.g., salmeterol; formoterol; bambuterol); inhaled corticosteroids (e.g., beclomethasone; budesonide; flunisolide; fluticasone; triamcinolone); leukotriene modifiers (e.g., montelukast; zafirlukast; zileuton); oral corticosteroids (e.g., prednisolone; prednisone; methylprednisolone); methylxanthines (e.g., theophyline); IgE inhibitors (e.g., omalizumab); cromolyn; and nedocromil. These drugs have all been used or suggested for use for asthmatics and dosages, duration of administration, and potential side effects are well known in the art. They may be used in any pharmaceutically acceptable form including any pharmaceutically acceptable salt form. The same or different drugs may be used for other conditions. Situations in which a second drug may be used will be described below in more detail.

As was described above, the inhaler 10 also includes a sensor/transmitter portion 14. As shown in FIGS. 1-4, the general arrangement of the inhaler 10 is such that the inhaler portion 12 is nested within and surrounded by the sensor/transmitter portion 14. One purpose of the sensor/transmitter portion 14 is to sense that a dose of medication has been dispensed and to communicate that fact to a remote monitoring station.

Many of the components of the sensor/transmitter portion 14 are contained within a housing 24, which may be plastic, metal, or some other durable material that protects the components from damage. However, protruding from the housing 24 and positioned so as to be adjacent but external to the inhaler portion 12 is a dose-dispensing sensor 26. In the illustrated embodiment, the dose-dispensing sensor 26 is essentially an electrical switch in the form of a depressable button. When the dose-dispensing sensor 26 is actuated (i.e., depressed), it establishes an electrical signal indicating that a dose of medication has been dispensed. The basic switch design is well known in the art and is described fully in US 20050172958 (see especially FIGS. 3A and 3B). In essence, the depression of the actuator moves a contact rod to a position where the switch is closed to allow current flow. After compression, the contact rod springs back to its original position opening the circuit and preventing current flow.

The canister 16 is coupled to the dose-dispensing sensor 26 of the illustrated embodiment by means of a cap or lip 28 that is sized to accommodate the top end of the canister 16 and is releasably secured thereto by means of one or more set screws 30. The cap or lip 28 is of sufficient diameter to overhang the canister 16. Thus, as the canister 16 is depressed, the cap or lip 28 pushes down on and actuates the dose-dispensing sensor 26. This simple mechanical coupling between the canister 16 and the dose-dispensing sensor 26 is robust and simple to use. However, in other embodiments, the dispensing of a dose may be sensed by other means, including magnetic sensors (e.g., Hall Effect sensors) and optical sensors.

The position of the dose-dispensing sensor 26 and the simple means by which it is coupled to the canister 16 to sense when a dose has been dispensed may have certain advantages. For example, an off-the-shelf standard inhaler may be used as the inhaler portion 12 of the inhaler 10. Additionally, the dose-dispensing sensor 26 is not within the flow pathway, where it might be fouled by medication particles or droplets. Moreover, the relatively large size of the components may make the sensor/transmitter portion 14 easier to assemble, maintain, and repair. Furthermore, in the event that the sensor/transmitter portion 14 should fail, the arrangement of the inhaler 10 is such that the patient may continue to dispense medication as normal; thus, mechanical or electrical failure would not prevent a patient from getting his or her medication.

Figure 3:
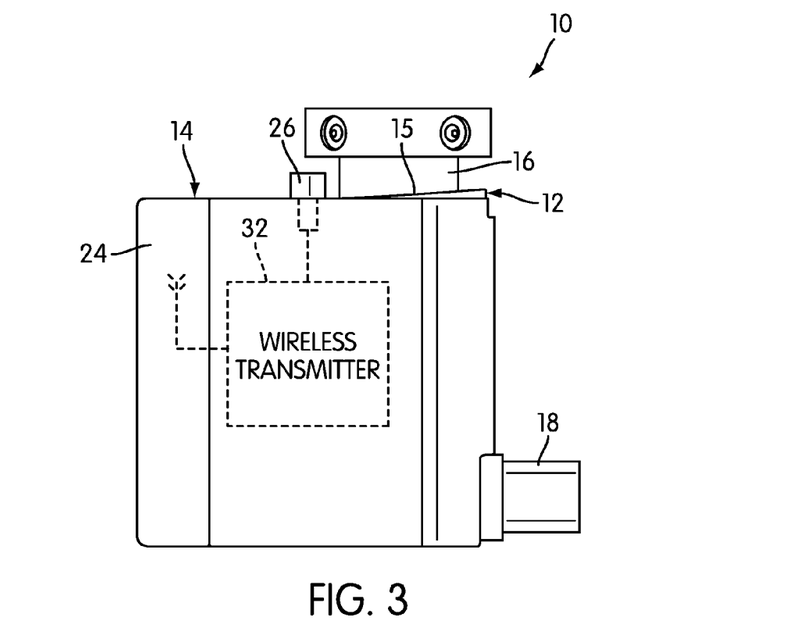

Also within the housing 24 and connected or coupled to the dose-dispensing sensor 26 is a wireless transmitter 32, which is shown schematically in the view of FIG. 3. The purpose of the wireless transmitter 32 is to transmit a signal indicating that a dose of medication has been administered to a remote monitoring station. (As will be explained below in more detail, that signal may, and usually will, contain additional information as well.)

The wireless transmitter 32 may be any sort of wireless transmitter known in the art, provided that it provides the capability to transmit from any place that the patient is likely to be. In the illustrated embodiment, the wireless transmitter 32 may be a conventional GSM cellular network transceiver, with associated components. In other embodiments, the wireless transmitter 32 may be adapted to transmit using substantially any frequency band or transmission protocols (e.g., CDMA, WiFi, WiMax, etc.).

The sensor/transmitter portion 14 may also include storage (e.g., random access memory, read-only memory, flash memory), and a central unit, such as a microprocessor, connected to the other components. An input/output (I/O) controller and appropriate connection ports may also be included in order to facilitate the process of programming the inhaler 10 or communicating with it at short range. Although not shown in the illustrated embodiment, the sensor/transmitter portion 14 may also be provided with a display screen, one or more indicator lights, or another means for communicating its status to the user. Additionally, to the extent desired, the sensor/transmitter portion 14 may also include one or more user inputs. The components of the sensor/transmitter portion 14 may be directly connected to one another, or data may be shared among the components using a data bus or another similar arrangement. Generally, the sensor/transmitter portion 14 would be powered by one or more batteries, space for which is provided in the housing 24.

It will be realized that although a microprocessor is one type of central unit that may be used in the sensor/transmitter portion 14 of the inhaler 10, other types of devices may be used. For example, some or all of the functions described here may be implemented in an application-specific integrated circuit (ASIC). In general, any type of device capable of performing the functions described in the present application may be used.

As was noted above, the wireless transmitter 32, and many of the other processing components of the sensor/transmitter portion 14, may be conventional components from a cellular telephone. Cellular telephones, or, to use a more general term, embedded devices, increasingly have the performance and capabilities of general-purpose computers. For example, U.S. Patent Application Publication No. 20060066731 illustrates a cellular telephone/embedded device architecture with significant processing power and most, if not all, of the functions of a general-purpose computer. These sorts of components are readily available, well known, and also provide the possibility for bidirectional communication in some circumstances.

In a relatively simple embodiment, an electrical signal from the dose-dispensing sensor 26 would be registered and recorded by the microprocessor or other central unit. Since the inhaler 10 may be actuated to dispense doses of medication several times in succession, a transmission reporting the dose(s) would generally be sent some predetermined amount of time after the last dose was administered. For example, a transmission reporting the dose(s) may be sent one minute after the last dose was dispensed. (In medical terms, a "dose" of a drug may comprise more than one puff or inhalation from an inhaler; however, the inhaler 10 would generally report in terms of the number of times that puffs were dispensed, even though a dose may properly comprise two or more puffs or actuations. Those units may be later be converted.)

The transmission itself may have any format or be encoded for transmission in any manner. Depending on the embodiment, the microprocessor or other central unit may add additional information to the transmission, such as the date and time the dose(s) were dispensed, and state information about the inhaler 10, such as the amount of battery power remaining Moreover, the inhaler 10 need not transmit only immediately after a dose has been administered. For example, in some embodiments, it may be advantageous to program the inhaler 10 to power up and transmit a signal once a day, or at some other predetermined interval, to confirm that it is still active and functional. In those embodiments, if an inhaler 10 fails to report in at its designated intervals, the patient may be contacted to determine what his or her situation is.

As those of skill in the art will realize, it is advantageous to have some means by which to identify each individual inhaler 10 if multiple inhalers 10 are in use within the same system. There are several ways in which that may be accomplished. In the illustrated embodiment, the inhaler 10 communicates via a standard cellular telephone network and therefore has a telephone number associated with it. Thus, any communication from the inhaler 10 will have a unique telephone number associated with it. In addition or alternatively, the microprocessor could add a unique identifier, such as a serial number, to the outgoing data transmission.

The inhaler 10 may also store a local copy of the dose administration information, and may be configured and adapted to display that information, either using output devices (e.g., a display screen or indicator lights) provided as a part of the sensor/transmitter module 14 of the inhaler 10 or through an external display or device. Moreover, should a transmission fail, the information may be stored for later transmission when service once again becomes available.

The precise amount of storage space and computing power provided as a part of the inhaler 10 and its sensor/transmitter portion 14 may depend, at least in part, on the precise functions that the inhaler 10 is tasked to perform. The above describes a relatively simple embodiment; however, in some embodiments, pattern analysis, detection, and two-way communication tasks may be performed in whole or in part by the inhaler 10.

Figure 6:
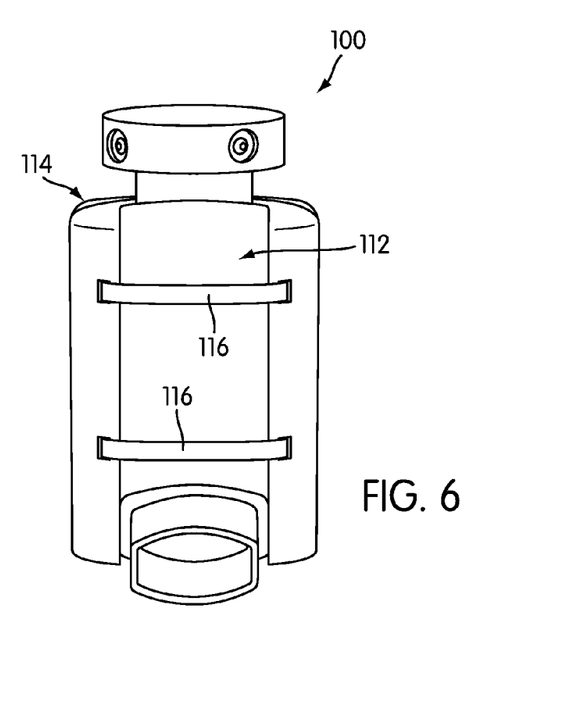
FIG. 6 is a perspective view of an alternate embodiment of the inhaler, in which the sensor/transmitter portion of the device may be attached to a conventional inhaler.

The form of the inhaler may vary considerably from embodiment to embodiment. For example, in the inhaler 10, the sensor/transmitter portion 14 is essentially permanently attached to the inhaler portion 12. In other embodiments, that may not be the case. For example, FIG. 6 is a perspective view of an inhaler 100 according to another embodiment of the invention. The inhaler 100 is substantially similar to the inhaler 10 of FIGS. 1-5, and those parts not described in detail here may be assumed to be the same or substantially the same; however, in the inhaler 100, the sensor/transmitter portion 114 is releasably connected to the inhaler portion 112 by way of semi-rigid plastic straps 116, such that the sensor/transmitter portion 114 may be detached from the inhaler portion 112. This embodiment may be particularly useful in retrofitting existing inhalers with a sensor/transmitter portion 114.

In some embodiments, the inhaler 10, 100 may be constructed and arranged to contain a second therapeutic agent, as described above, to be dispensed to the patient under certain conditions, particularly when a disease exacerbation is detected. That second agent may be stored, for example, in a separate medication reservoir for inhalation. If the second therapeutic agent is in tablet or caplet form, it may be stored in a compartment in the inhaler 10, 100. Depending on the embodiment, the patient may be able to open that compartment at will, or it may open only in response to a signal sent by a medical professional authorized to dispense the drug. In further embodiments, the inhaler 10, 100 may be programmed to dispense a mixed dose of two inhaled medications depending on the patient's particular condition. Alternately, the patient may simply be provided with instructions regarding how to titrate or apportion the doses of the first and second therapeutic agents. In the simplest embodiments, the patient may be provided with another inhaler or other dispensing device for the second therapeutic agent. That inhaler may or may not be an inhaler 10, 100 according to the present invention.

Instrumented metered-dose inhalers according to embodiments of the present invention may be used simply to record when doses of a medication are administered and to confirm that a patient is complying with physician orders. However, such instrumented metered-dose inhalers are most advantageously used not only to perform those basic tasks, but also to predict, based on drug usage patterns, when an acute attack or exacerbation is likely to occur.

Studies show that increased use of short-acting inhaled beta$_2$ agonists among asthma patients is more common before an exacerbation and before asthma-related death (Chan-Yeung, et al., *Am. J. Respir. Crit. Care Med.* 154: 889-93 (1996); Hessel, et al., *Ann. Allergy Asthma Immunol* 83:362-368 (1999); Cairns, *Clin. Chest Med.* 27: 99-108 (2006)). Prospectively, albuterol use of greater than 4 times a day was found to have a relative risk of 1.33 for an exacerbation and nocturnal symptoms had a relative risk of 1.79 (Gibson, et al., *Ann. Intern. Med.* 123:488-492 (1995)). Thus, both the amount of drug usage and the time of usage may be important indicators of an impending exacerbation. Exacerbations usually respond well to additional medication such as corticosteroids and, if treatment is initiated early enough, it may be possible to avert the attack or, at the least, reduce its severity. Unfortunately, patients may not recognize warning signs either because drug usage escalates gradually and they are preoccupied with other matters or, in some cases, because their cognitive abilities are impaired, e.g., due to age or illness.

Thus, aspects of the present invention provide systems and methods for identifying exacerbation patterns—patterns of medication use that would tend to indicate that a disease exacerbation, or another other form of deterioration or complication, is imminent—and notifying both a physician or other medical professional and the patient. Additionally, as was noted briefly above, systems and methods according to embodiments of the invention may provide for bi-directional (i.e., two-way) communication with the patient for diagnostic or interventional purposes when exacerbations or complications occur.

Figure 7:
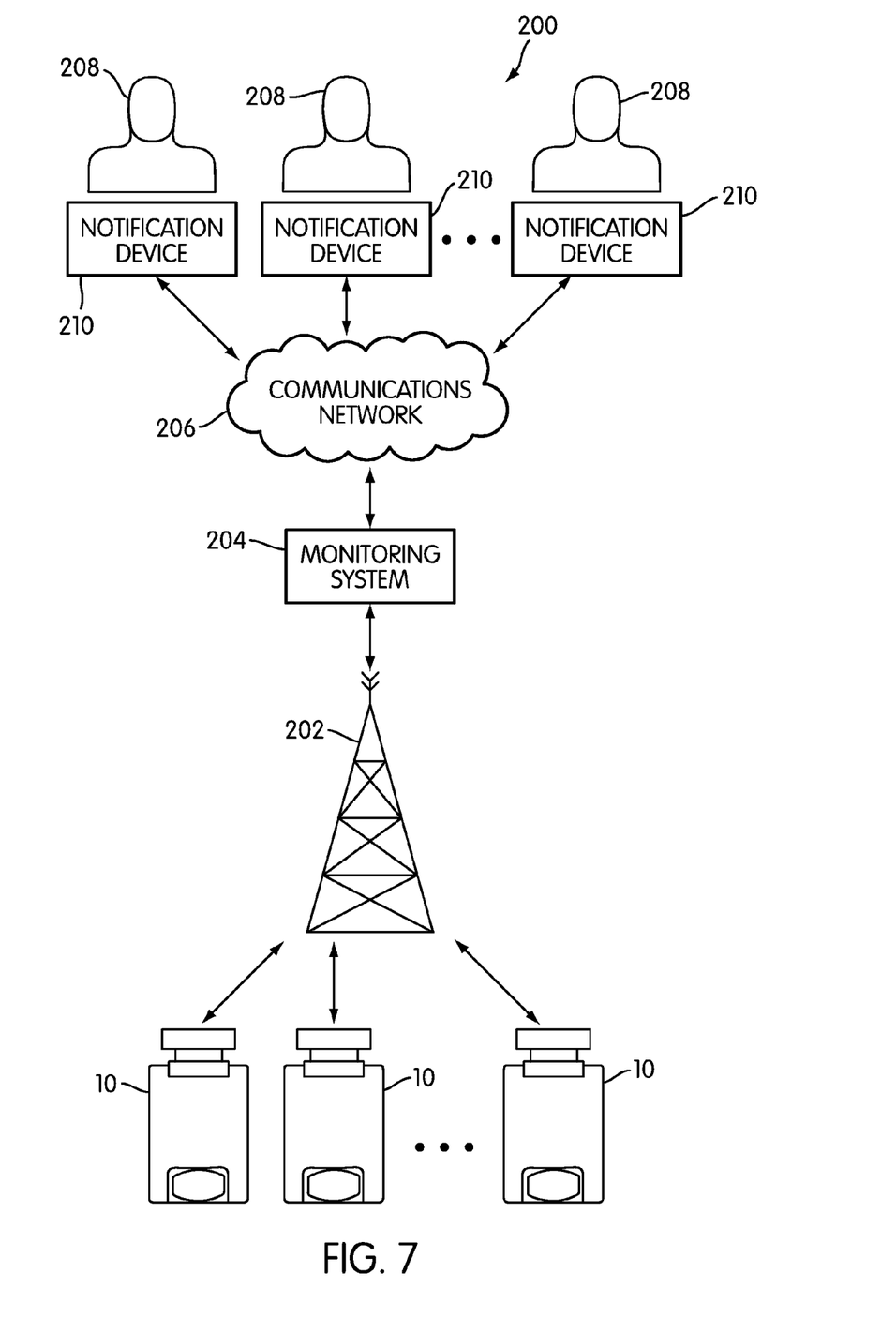
FIG. 7 is an illustration of a system for monitoring patient inhaled medication usage and disease progression according to another embodiment of the invention.

FIG. 7 is a schematic illustration of a system, generally indicated at 200, according to one embodiment of the invention. In system 200, a plurality of inhalers 10 are shown, each presumably belonging to a different patient. It should be understood that although inhalers 10, 100 according to embodiments of the present invention are shown as a part of system 200, other types of instrumented inhalers may be used for at least some of the functions and tasks described with respect to system 200. If the inhalers that are used as part of system 200 have additional features not found in the inhalers 10, 100 described here, those features may be taken advantage of. For example, data from the flowmeter of the inhaler disclosed in US 20050172958 may be taken into account in determining whether or not an exacerbation pattern exists.

Each of the inhalers 10, 100 communicates wirelessly with a remote transceiver 202. In some embodiments, that remote transceiver 202 may be a cell or base station in a cellular telephone network.

The remote transceiver 202 is in communication with a monitoring system 204. Although not shown in FIG. 7, the remote transceiver 202 would generally be connected to a communications network of its own, and may communicate with the monitoring system 204 indirectly through a number of intermediary systems and elements. For example, traffic from the remote transceiver 202 may pass through the proprietary network of a cellular communications network and through a gateway to the Internet, through which it reaches the monitoring system 204.

The monitoring system 204 itself is a system, or a plurality of interconnected, interoperating systems, that are charged with monitoring the transmissions from the inhalers 10, 100, performing predictive analysis to determine when patients are experiencing exacerbation patterns that might be indicative of forthcoming exacerbations or complications, and distributing notifications regarding patient status to the appropriate decision making or disease-management medical personnel. The monitoring system 204 also keeps the primary set of records associated with the system 200 and, for example, would usually be programmed with a database that is capable of associating incoming traffic from particular inhalers with patient information, including the patient's name, physician or other attending medical professional, contact information for the patient and relevant medical professionals, pertinent medical history, name of the patient's preferred pharmacy, and any other information deemed relevant. The database may, for example, be indexed by the cellular telephone number of the patient's inhaler 10, 100, or by some other kind of unique identifier assigned to the patient or his or her inhaler 10, 100.

The monitoring system 204 communicates through a communications network 206 to notification devices 210 associated with the physicians or other medical professionals 208 attending the patients. The notification devices 210 may be cellular telephones, pagers, alphanumeric pagers, personal digital assistants, smartphones, computers, or any other kind of device or system capable of receiving notification messages directly or indirectly from the monitoring system 204 and providing the medical professionals 208 with those notifications. Depending on the situation, particularly if there are relatively few inhalers 10, 100 to be monitored, one of the notification devices 210 could also serve as the monitoring system 204.

The type of notification that is sent will depend on the types of notification devices 210 that are in use, as well as the preferences of the individuals using the system. As one example, the monitoring system 204 may send e-mails to the attending physicians, disease management nurses, or other responsible medical professionals detailing the condition of each patient and whether or not that patient is likely to be experiencing an exacerbation pattern, either on a regular basis (e.g., daily), when a pattern requiring immediate notification is detected, or both. This will be described below in more detail.

In some embodiments, the monitoring system 204 may also be used to convey messages or instructions back to the inhalers 10, 100 and the respective patients. For example, as was described above, in some embodiments, the patient may be instructed to take a second therapeutic agent to manage an exacerbation or avert an impeding exacerbation. Those instructions could come from or through the monitoring system 204. Additionally, the monitoring system 204 could, if the inhalers 10, 100 are appropriately equipped with a display and input mechanism, send questionnaires or other queries for the users to answer, in order to assess whether or not the pattern detected by the monitoring system 204 is corroborated by other signs or symptoms. For example, patients could be asked to take an asthma questionnaire, in which case the questions may be sent by the monitoring system 204 to the inhaler 10, 100 of the patient in question. Alternatively, appropriate questionnaires and other contingency protocols and instructions may be stored in the inhalers 10, 100 and activated by a communication from the monitoring system 204.

In describing the elements and functions of system 200, it may thus be said that the inhalers 10, 100 transmit their data to a remote station, that data is processed, and appropriate notifications are made if the patient's condition or pattern of medication usage so warrants. However, the term "remote station" is a general one, and may encompass any one of or all of the elements 202, 204, 210 that receive and process signals from the inhalers 10, 100. The precise nature of the elements that receive and process signals from the inhalers 10, 100 may vary from embodiment to embodiment; the illustration of FIG. 7 is but one example. Those of skill in the art will also realize that although certain tasks and capabilities have been ascribed to certain elements of system 200, as a practical matter, at least some functions of system 200 may be equally well performed by a number of elements in system 200. For example, some of the tasks ascribed to the monitoring system 204, such as the detection of exacerbation patterns, may be equally well performed by the inhalers 10, 100 themselves in some embodiments.

As was noted above, one function of system 200 is to detect exacerbation patterns. The description above points out two such specific exacerbation patterns for albuterol: use greater than 4 times a day, and nocturnal use of the drug when the patient in question would normally be sleeping. More generally, exacerbation patterns may involve any or all of the following: increased frequency of use (e.g., more actuations per 24 hour period or per 72 hour moving window); increased nocturnal frequency (e.g., between 10 PM and 6 AM) in a patient who would normally be sleeping; and increased stacking of doses (e.g., more than two successive actuations in less than 10 minutes). Additionally, seasonal usage may be taken into account. For example, a patient's usage on a weekly basis may be determined, seasons during which the patient tends to experience exacerbations could be identified, and interventions may be planned for the next season.

Although absolute thresholds may be used in determining whether or not a particular patient is experiencing an exacerbation pattern, it may be more advantageous to establish which usage patterns qualify as exacerbation patterns for each individual patient. That could be done, for example, by tracking the patient's usage prior to a known exacerbation (e.g., an emergency room or physician visit for acute treatment) and using that data to establish what usage patterns qualify as exacerbation patterns. In some embodiments, the inhalers 10, 100 may auto-calibrate (or be calibrated by the monitoring system 204) for the patient's baseline drug usage by averaging the patient's drug usage over a defined period of time, and defining an exacerbation pattern to be any pattern that deviates from the average by more than a certain amount. As an example, an increase in the frequency of administration of a short acting $beta_2$ agonist of 20-100% measured over a period of 3 to 10 days would generally be considered an exacerbation pattern, and may also be grounds for administering the second therapeutic agent, as described above.

The above gives a broad overview of the types of exacerbation patterns that may be detected. However, not all exacerbation patterns are necessarily equally well correlated to disease exacerbations; some exacerbation patterns may be more strongly indicative of an impending exacerbation, and some exacerbation patterns may be indicative of a more severe exacerbation. Systems and methods according to embodiments of the present invention may take these differences into account.

Figure 8:
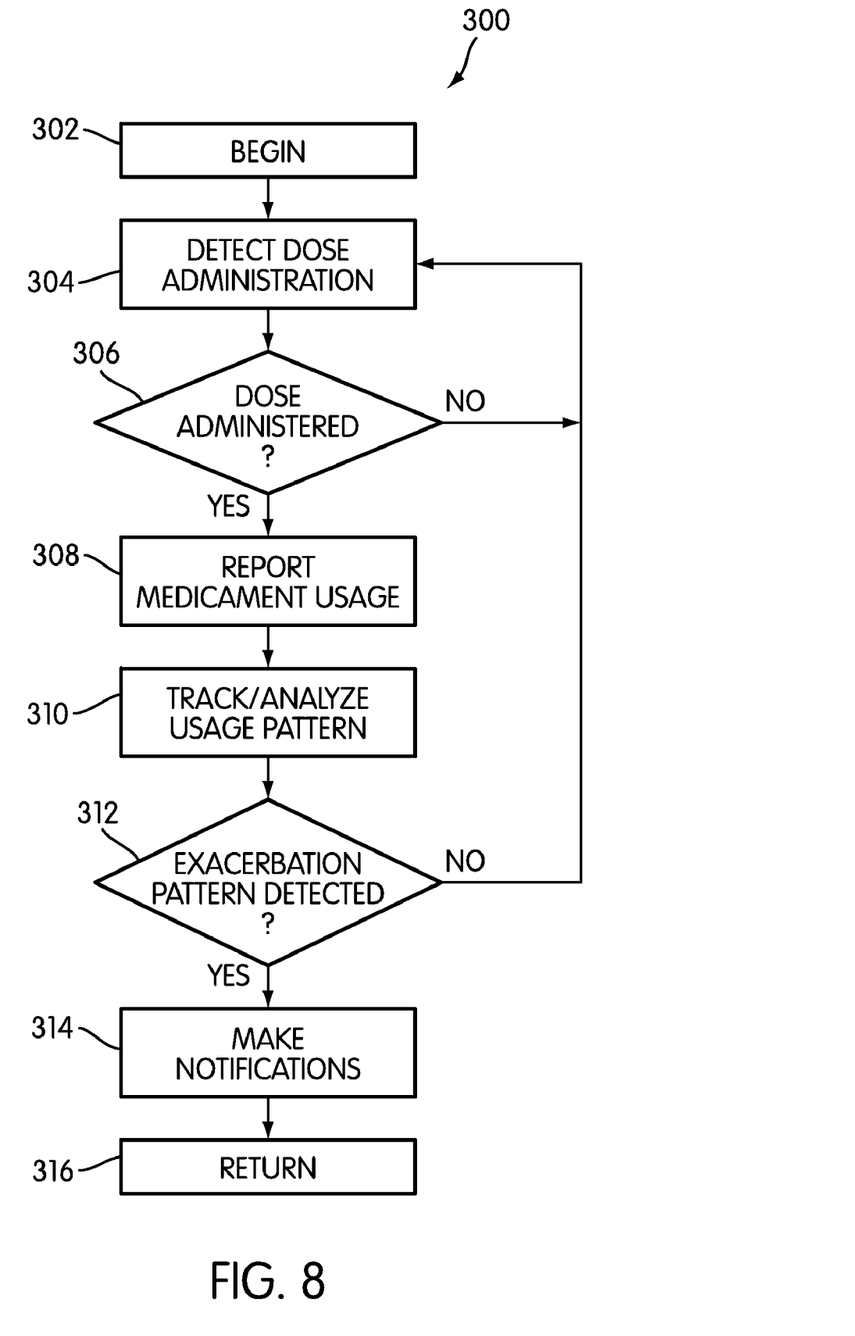
FIG. 8 is an illustration of a method for detecting and predicting disease exacerbations according to yet another embodiment of the invention.
Figure 9:
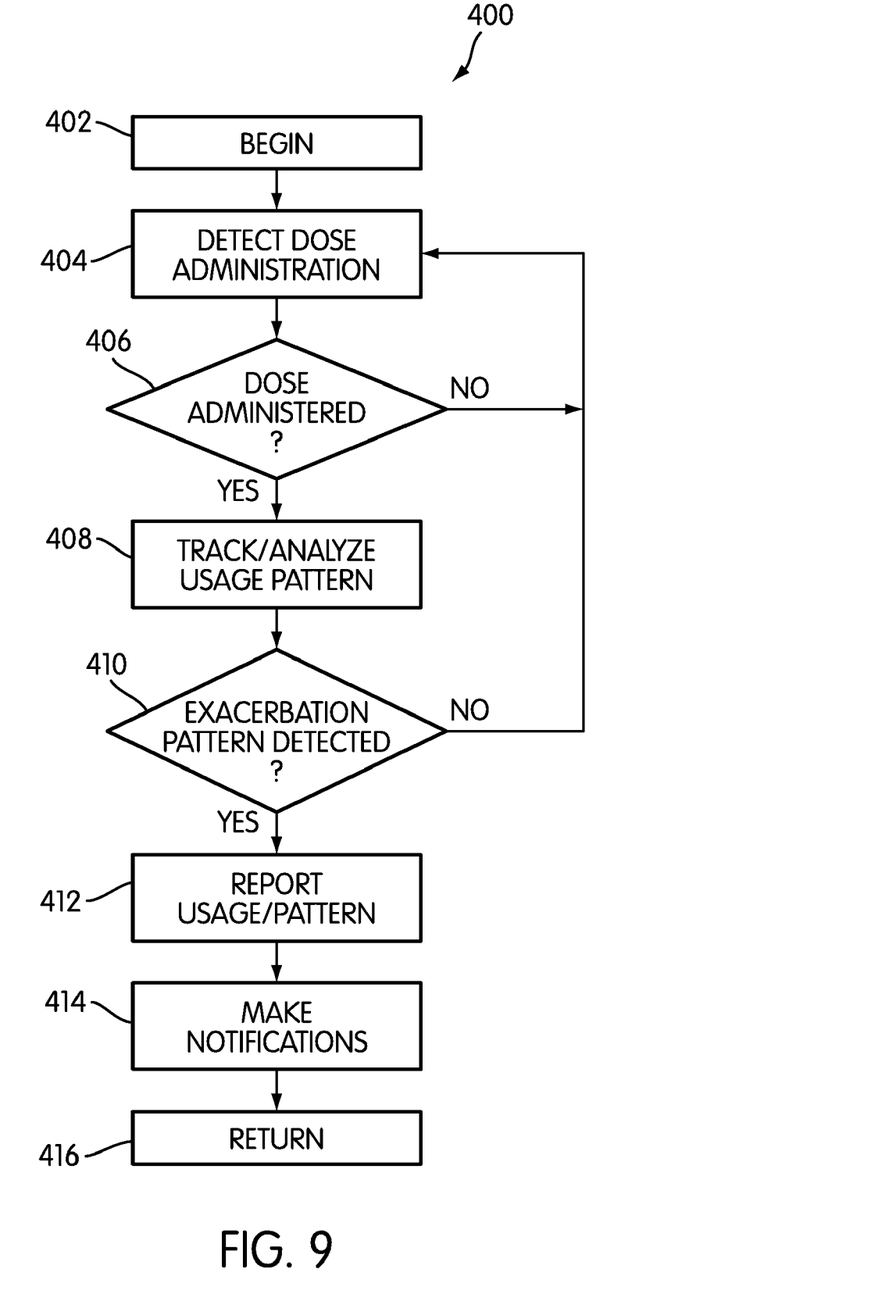
FIG. 9 is an illustration of another method for detecting and predicting disease exacerbations.

FIGS. 8 and 9 are flow diagrams illustrating two similar methods of detecting and predicting disease exacerbations according to embodiments of the invention. Method 300 of FIG. 8 illustrates a scenario in which the inhaler 10, 100 does not have significant processing capabilities, and thus, does not perform any pattern analysis tasks. Method 400 of FIG. 9 illustrates an opposite scenario in which the inhaler 10, 100 does have significant processing power. As those of skill in the art will realize, methods 300 and 400 represent opposite ends of a spectrum, and methods according to embodiments of the invention may apportion functions or tasks to different components of the system in many different ways. Moreover, both methods illustrate only routine cycles of use; other calibration, reporting, and interactive tasks, particularly those described above, may be included in the methods.

Method 300 begins at 302 and continues with task 304, in which the inhaler 10, 100 detects whether or not a dose of medication has been administered. If a dose has been administered (task 306:YES), method 300 continues with task 308; if a dose has not been administered (task 306:NO), method 300 returns to task 304. The inhaler 10, 100 may remain in this loop for a long period of time, and may be programmed to power down into a "standby" or "sleep" mode accordingly, shutting down the transmitter or other components until needed in order to conserve power.

When a dose has been administered (task 306:YES), the inhaler 10, 100 powers up and transmits an appropriate report to its remote station, as described above. Typically, that report would reach the monitoring system 204, which would timestamp and store the information in its database before proceeding with task 310, in which the patient's usage patterns are tracked and analyzed to determine whether an exacerbation pattern exists.

In determining whether an exacerbation pattern exists, any of the criteria or methods described above may be employed, and any other medically reasonable criteria may also be employed. Other criteria may be found in the literature. More generally, additional guidance regarding patient monitoring and monitoring systems may be found in Tovar et al. (*Ann.*

*Pharmacother.* 38(1):126-133 (2004)); Marosi et al. (*J. Asthma* 38(8):681-690 (2001)); Martin et al. (*J. Allergy Clin. Immumol.* 103(3 Pt. 1):535-536 (1999)) and, especially US 20050172958.

Task 310 need not always be performed every time incoming data is received. Rather, it may be delayed or performed on a regular schedule (e.g., every 4-6 hours, every day, etc.). However, the more often task 310 is performed, the more likely it is that an exacerbation pattern will be detected quickly if present, and the more likely it will be that the patient receives timely intervention. Method 300 continues with task 312, a decision task.

If no exacerbation pattern is detected (task 312:NO), the monitoring system 204 may simply wait for the next packet of incoming data from an inhaler 10, 100. In terms of FIG. 8, method 300 returns to task 304. If an exacerbation pattern is detected (task 312:YES), method 300 continues with task 314, in which appropriate notifications (e.g., by e-mail to a physician or disease management nurse) are made.

As shown in FIG. 7, illustrating system 200, many inhalers 10, 100 may be in the field at any one time, and many may be in communication with the monitoring system 204 at any one time. Thus, method 300 may be executed may times concurrently or in parallel. If method 300 is executed multiple times and several patients have exacerbation patterns for which notifications are to be sent to the same physician or other destination, the notifications may be concatenated to the extent practicable. If multiple patients are covered by a single notification, their situations may prioritized so that the most serious or potentially serious condition is most readily seen. Patients whose usage is normal may also be included in the notifications, for the sake of completeness. For example, a physician may receive an e-mail similar to the following:

| PHYSICIAN: Jane Q. Doe, M.D. | | |
| --- | --- | --- |
| CONDITION | PATIENT | REASON/COMMENT |
| RED | John Smith | Usage up 50% in last 3 days |
| ORANGE | Jane Jones | Known seasonal problem |
| YELLOW | David James | Administered dose at 2:43AM |
| GREEN | Larry Zeller | Within normal limits |

Although e-mail is given as one specific example of a mode of notification, notifications may also be posted to a public or private World Wide Web site, entered directly into an electronic medical records system, or delivered in any other convenient fashion. Additionally, a notification signal may be sent back to the inhaler 10, 100, in order to notify the patient that a possible problem has been detected. Method 300 terminates at task 316.

Method 400 of FIG. 9 is similar in many respects to method 300, and the description of method 300 above is thus applicable to method 400 unless otherwise indicated. Method 400 begins at task 402 and continues with tasks 404 and 406, which are substantially similar to tasks 304 and 306 of method 300.

However, in method 400, if a dose has been administered (task 406:YES), method 400 continues with task 408, in which the patient's usage pattern is analyzed. As was described above, in method 400, the inhaler 10, 100 is assumed to have substantial processing power, and thus performs at least some analysis tasks. Task 408 of method 400 generally corresponds with task 310 of method 300, although the inhaler 10, 100 may perform only a portion of the "full" analysis, depending on its capabilities.

Following task 408, method 400 continues with task 410, a decision task. In task 410, if an exacerbation pattern is detected (task 410:YES), method 400 continues with task 412; if not (task 410:NO), method 400 may return to task 404. (It should be noted that the inhaler 10, 100 will report that a dose has been administered regardless of whether or not an exacerbation pattern was detected in most embodiments. In those embodiments, it may be desirable or advantageous to report that no exacerbation pattern was detected in order to save time and processing power on the monitoring system 204. However, in other embodiments, the monitoring system 204 may confirm the results reached by the inhaler 10, 100 regardless of the outcome of task 408.)

Tasks 412 is somewhat similar to task 308 of method 300; the inhaler 10, 100 reports to the monitoring system 204. However, in task 412, the inhaler 10, 100 may also report the results of any analysis that was performed, in addition to the bare fact that a dose was dispensed. Method 400 continues with task 414, which is essentially the same task task 314 of method 300, and terminates and returns at task 416.

Any method according to an embodiment of the present invention may be encapsulated in one or more sets of machine-readable instructions that are interoperable with a machine or machines to perform the tasks of the method. Machine-readable media include magnetic and optical media, as well as FLASH drives, read-only memory, and any other sort of machine-readable storage medium known in the art.

As was described above, devices, systems, and methods according to embodiments of the invention will be of particular use to patients with respiratory diseases, such as asthma and chronic obstructive pulmonary disease. However they may also be used for patients with cystic fibrosis, non-cystic fibrosis bronchiectasis, forms of interstitial lung disease, reactive airways disease, occupational lung disease, congestive heart failure, and in patients that have received a solid organ transplant or bone marrow transplant.

All references cited herein are fully incorporated by reference. Having now fully described the invention, it will be understood by one of skill in the art that the invention may be performed with a wide range of modifications and changes and under a broad range of conditions, without affecting the spirit or scope of the invention or any embodiment thereof.

What is claimed is:
1. A metered dose inhaler, comprising:
a) an inhaler portion including:
   i) a medication reservoir compartment constructed and adapted to engage a medication reservoir or to contain medication;
   ii) a mouthpiece; and
   iii) a flow pathway opening into and connecting the medication reservoir compartment and the mouthpiece so as to deliver a metered dose of a medication from the medication reservoir compartment to the mouthpiece when the inhaler portion is actuated to dispense a metered dose of the medication; and
b) a sensor/transmitter portion including:
   i) a dose-dispensing sensor positioned external to the inhaler portion, the dose-dispensing sensor being coupled to the inhaler portion such that when the inhaler portion is actuated to dispense the dose of the medication, the dose-dispensing sensor establishes a signal in response thereto; and
   ii) a wireless transmitter connected to the dose-dispensing sensor, the wireless transmitter being constructed and arranged to accept the signal from the dose-dis- pensing sensor and transmit a signal indicating that a dose has been dispensed to a remote station.

2. The metered dose inhaler of claim 1, wherein the inhaler portion further comprises a movable part constructed and arranged to move between:
(1) a dispensing position in which the inhaler portion is actuated to dispense a dose of the medication; and (2) a non-dispensing position in which medication does not flow from the medication reservoir compartment into the mouthpiece, the movable part being biased toward the non-dispensing position.

3. The metered dose inhaler of claim 2, further comprising a coupling element connected to the movable part, the coupling element being constructed and arranged to couple the dose-dispensing sensor to the movement of the movable part such that the dose-dispensing sensor is activated when the movable part moves into the dispensing position.

4. The metered dose inhaler of claim 3, wherein a medication reservoir installed in the medication reservoir compartment serves as the movable part.

5. The metered dose inhaler of claim 4, wherein the dose-dispensing sensor comprises a mechanical pressure switch that is activated when depressed.

6. The metered dose inhaler of claim 5, wherein the coupling element comprises a cap or lip secured to the medication reservoir such that the cap or lip will contact and depress the dose-dispensing sensor when the medication reservoir is in the depressed, dispensing position.

7. The metered dose inhaler of claim 1, wherein the wireless transmitter is a cellular network wireless transmitter.

8. The metered dose inhaler of claim 1, further comprising a microprocessor connected between the dose-dispensing sensor and the wireless transmitter.

9. The metered dose inhaler of claim 8, wherein:
a) the microprocessor controls the wireless transmitter to transmit the signal indicating that the dose has been dispensed at a predetermined interval of time after the dose has been dispensed; and
b) the signal indicating that the dose has been dispensed comprises the amount of the dose or number of times that the inhaler portion was actuated, and the time that the dose was dispensed.

10. The metered dose inhaler of claim 1, wherein the inhaler portion nests within the sensor/transmitter portion.

11. The metered dose inhaler of claim 1, wherein the sensor/transmitter portion is releasably secured to the inhaler portion.

12. The metered dose inhaler of claim 6, wherein the wireless transmitter is a cellular network wireless transmitter.

13. The metered dose inhaler of claim 6, further comprising a microprocessor connected between the dose-dispensing sensor and the wireless transmitter.

14. The metered dose inhaler of claim 13, wherein:
a) the microprocessor controls the wireless transmitter to transmit the signal indicating that the dose has been dispensed at a predetermined interval of time after the dose has been dispensed; and
b) the signal indicating that the dose has been dispensed comprises the amount of the dose or number of times that the inhaler portion was actuated, and the time that the dose was dispensed.

15. The metered dose inhaler of claim 14, wherein the inhaler portion nests within the sensor/transmitter portion.

16. The metered dose inhaler of claim 14, wherein the sensor/transmitter portion is releasably secured to the inhaler portion.

* * * * *